US008959664B2

(12) United States Patent
Johnson et al.

(10) Patent No.: US 8,959,664 B2
(45) Date of Patent: Feb. 24, 2015

(54) HARNESS WEBBING PROTECTION SYSTEM

(75) Inventors: Andrew P. Johnson, St. Paul, MN (US); Paul M. Goudreau, St. Paul, MN (US)

(73) Assignee: D B Industries, LLC, Red Wing, MN (US)

( * ) Notice: Subject to any disclaimer, the term of this patent is extended or adjusted under 35 U.S.C. 154(b) by 1470 days.

(21) Appl. No.: 12/367,853

(22) Filed: Feb. 9, 2009

(65) Prior Publication Data

US 2010/0200329 A1 Aug. 12, 2010

(51) Int. Cl.
*A61F 5/02* (2006.01)
*A62B 35/00* (2006.01)

(52) U.S. Cl.
CPC .................................. *A62B 35/0025* (2013.01)
USPC ..................................................... 2/44; 182/3

(58) Field of Classification Search
USPC ............... 2/464, 455, 102, 95, 97, 44, 45, 94, 2/310, 311, 327, 328, 267; 182/3; 482/69
See application file for complete search history.

(56) References Cited

U.S. PATENT DOCUMENTS 1,784,162 A 11/1929 Smith
2,817,393 A * 12/1957 Mitchell ....................... 297/484
3,957,282 A 5/1976 Finnigan
4,619,468 A 10/1986 Spill
4,795,190 A 1/1989 Weightman et al.
5,108,152 A 4/1992 Reilly et al.
5,131,490 A 7/1992 Bell
5,329,884 A 7/1994 Bell
5,410,755 A * 5/1995 Obujen ............................. 2/465
5,540,188 A 7/1996 Heinrichs
5,551,082 A * 9/1996 Stewart et al. .................... 2/465
5,642,842 A * 7/1997 Taras ............................ 224/250
5,746,013 A 5/1998 Fay, Sr.
5,957,091 A 9/1999 McDonald et al.
6,253,874 B1 7/2001 Casebolt et al.
6,315,007 B1 11/2001 Mohamed et al.

(Continued)

FOREIGN PATENT DOCUMENTS

CA 2040951 C 11/1993
DE 299 19 016 U1 12/1999

(Continued)

OTHER PUBLICATIONS

Edge Series Harness Features, Guardian Fall Protection, www.guardianfall.com.

(Continued)

*Primary Examiner* — Khoa Huynh
*Assistant Examiner* — Anna Kinsaul
(74) *Attorney, Agent, or Firm* — IPLM Group, P.A.

(57) ABSTRACT

A webbing protection system is provided. The webbing protection system includes at least one pad portion and at least one protective member. The at least one pad portion has a first pad surface and a second pad surface. The first pad surface of each pad portion is configured to engage a portion of a body of a user. The second pad surface of each pad portion has at least one pad channel guide. Each protective member has at least one raised portion. Each protective member is coupled to an associated pad portion such that the raised portion of the protective member is aligned with an associated pad channel guide of the associated pad portion to provide a first guide path for the first webbing. Each protective member provides wear and abrasion protection for the first webbing proximate the guide path.

7 Claims, 18 Drawing Sheets

(56) References Cited

U.S. PATENT DOCUMENTS

| | | | | |
|---|---|---|---|---|
| D454,986 | S | 3/2002 | Casebolt et al. | |
| 6,378,465 | B1 | 4/2002 | Austin | |
| 6,446,273 | B1 | 9/2002 | Gillen et al. | |
| 6,520,290 | B1 | 2/2003 | Carter | |
| 6,969,548 | B1 * | 11/2005 | Goldfine | 428/159 |
| 6,971,476 | B2 | 12/2005 | Wolner et al. | |
| 7,100,216 | B2 * | 9/2006 | Matechen et al. | 2/455 |
| 7,818,820 | B2 * | 10/2010 | Tsujimoto | 2/310 |
| 2005/0205356 | A1 | 9/2005 | Velasco, Jr. | |
| 2006/0113147 | A1 * | 6/2006 | Harris | 182/3 |
| 2011/0017546 | A1 * | 1/2011 | Nichols, Jr. | 182/3 |

FOREIGN PATENT DOCUMENTS

| | | | |
|---|---|---|---|
| EP | 0 508 278 | A1 | 10/1992 |
| WO | WO 2005/025676 | A1 | 3/2005 |
| WO | WO 2007/035837 | A2 | 3/2007 |

OTHER PUBLICATIONS

Skylotec, ARG 50 Wind Click. http://skylotec-katalog.de/show_item.php?item=ARG%2050%20WIND%20CLICK Jan. 16, 2009.

Bacou-Dalloz, "Miller Ultra Harnesses". Product Brochure for DuraFlex Ultra and DuraFlex Python Ultra. Sep. 2003, 2 pages.

International Search Report from PCT/US2010/023281 mailed Jun. 25, 2010.

Mine Safety Appliances Company, "Take the TechnaCury Challenge." [online] [retrieved on Aug. 28, 2003] retrieved from the internet at <http://www.technacurv.com/>, 4 pages.

MSA Fall Protection Catalog. "Replaceable shoulder accessory pad, part No. 10028444." 2001-2002. vol. 3, pp. 1, 17 and 23.

Order dismissing the copending litigation in the United States District Court, District of Minnesota, *D B Industries, Inc. d/b/a DBI/SAVA* v. *Alexander Andrew, Inc. and Custom Leathercraft Mfg. Co., Inc. d/b/a FallTech*, Civil Action No. 05-CV-2806 (JMR/FLN).

Protecta International, "Removable Shoulder Pads for Full Body Harness" AK005A Technical Specifications. PTSB/OSB-FBH-FBHA/AK005A/REV. Nov. 2001, 2 pages.

Protecta International, "Silverback Standard Full body Harness AB2001A" [online] [retrieved online Nov. 20, 2003] retrieved from the internet <http://64.78.52.127/americas/catalog/product_detail.asp>, 1 page.

Rose Manufacturing Company, replaceable shoulder accessory pad, part No. 10028444, date unknown, front view of the replaceable shoulder pad with a safety harness connected thereto.

Rose Manufacturing Company, replaceable shoulder accessory pad, part No. 10028444, date unknown, front view of the replaceable shoulder pad with the lower left hook and loop fastener in an open position.

Rose Manufacturing Company, replaceable shoulder accessory pad, part No. 10028444, date unknown, front view of the lower left hook and loop fastener in an open position.

Rose Manufacturing Company, replaceable shoulder accessory pad, part No. 10028444, date unknown, side view of the upper right portion of the replaceable shoulder pad.

Rose Manufacturing Company, replaceable shoulder accessory pad, part No. 10028444, date unknown, rear view of the replaceable shoulder pad.

Rose Manufacturing Company, replaceable shoulder accessory pad, part No. 10028444, date unknown, cross-section view of the replaceable shoulder pad.

* cited by examiner

HARNESS WEBBING PROTECTION SYSTEM

BACKGROUND

Safety harnesses used for fall prevention and fall arrest employ webbing or straps that are secured around a user's body. In use, a harness is attached to a lanyard, lifeline or similar connecting means that is in turn attached to a support structure. If the user slips, the straps of the harness and the connecting means prevent the worker from falling to the ground. Hence, the structural integrity of the straps and the stitching that holds the straps together and to connectors such as buckles are imperative for proper functioning of the fall protection harness.

For the reasons stated above and for other reasons stated below which will become apparent to those skilled in the art upon reading and understanding the present specification, there is a need in the art for a device to protect the webbing or stitching in an effective and efficient manner.

SUMMARY OF INVENTION

The above-mentioned problems of current systems are addressed by embodiments of the present invention and will be understood by reading and studying the following specification. The following summary is made by way of example and not by way of limitation. It is merely provided to aid the reader in understanding some of the aspects of the invention.

In one embodiment, a webbing protection system is provided. The webbing protection system includes at least one pad portion and at least one protective member. The at least one pad portion has a first pad surface and a second pad surface. The first pad surface of each pad portion is configured to engage a portion of a body of a user. The second pad surface of each pad portion has at least one pad channel guide. Each protective member has at least one raised portion. Each protective member is coupled to an associated pad portion such that the raised portion of the protective member is aligned with an associated pad channel guide of the associated pad portion to provide a first guide path for the first webbing. Each protective member provides wear and abrasion protection for the first webbing proximate the guide path.

BRIEF DESCRIPTION OF THE DRAWINGS

The present invention can be more easily understood and further advantages and uses thereof more readily apparent, when considered in view of the detailed description and the following figures in which:

FIG. 10C is a side view of the protective member of FIG. 9.

In accordance with common practice, the various described features are not drawn to scale but are drawn to emphasize specific features relevant to the present invention. Reference characters denote like elements throughout Figures and text.

DETAILED DESCRIPTION

In the following detailed description, reference is made to the accompanying drawings, which form a part hereof, and in which is shown by way of illustration specific embodiments in which the inventions may be practiced. These embodiments are described in sufficient detail to enable those skilled in the art to practice the invention, and it is to be understood that other embodiments may be utilized and that mechanical changes may be made without departing from the spirit and scope of the present invention. The following detailed description is, therefore, not to be taken in a limiting sense, and the scope of the present invention is defined only by the claims and equivalents thereof.

Figure 1:
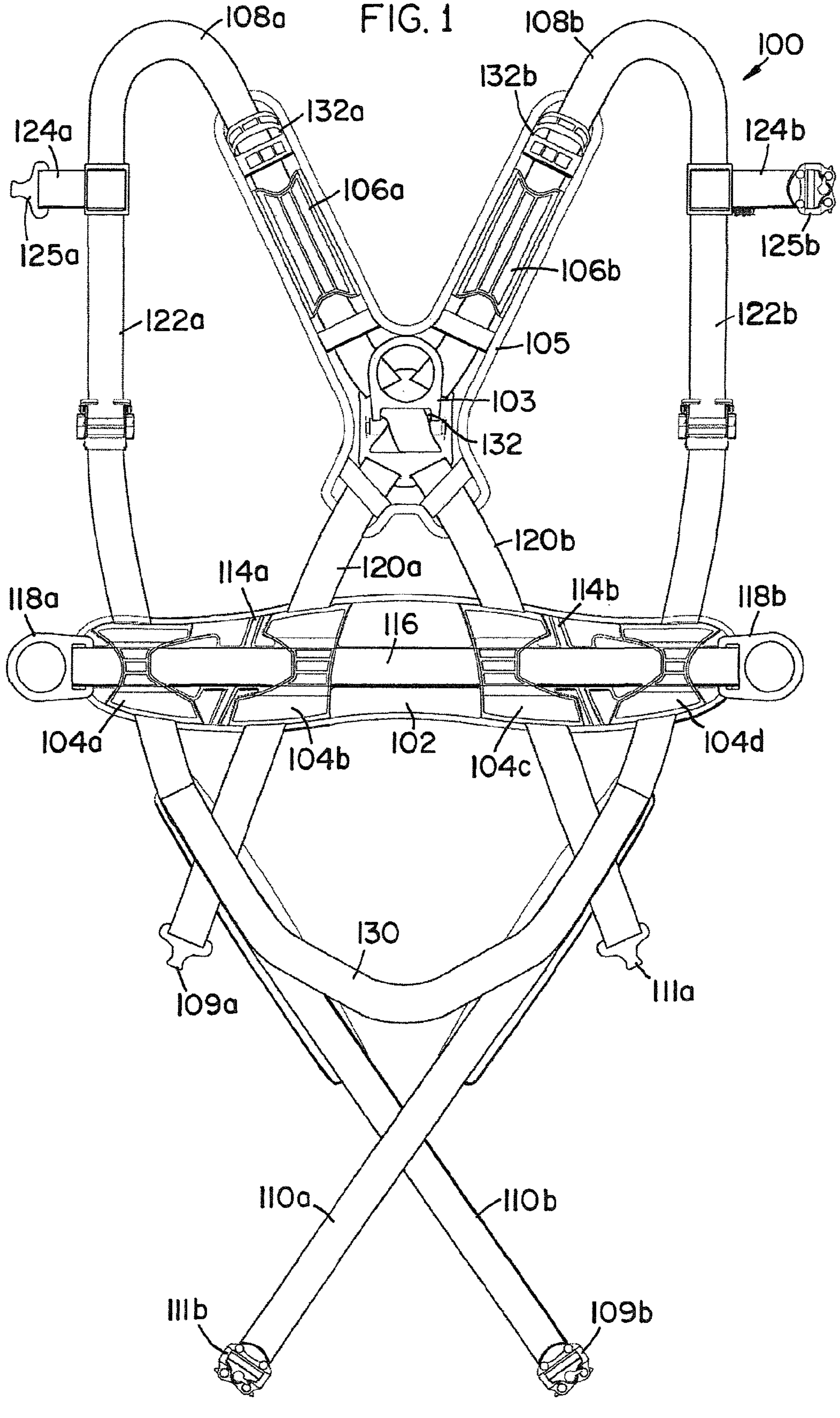
FIG. 1 is a rear view of a harness of one embodiment of the present invention.

Embodiments of the present invention provide a device that prevents wearing of the straps and the stitching in areas of the fall harness that are prone to wear. In particular, in embodiments, protective members provide protection for the straps from wear and abrasions. Embodiments also provide for the routing of straps. FIG. 1 illustrates a rear view of a harness 100 of one embodiment of the present invention. As illustrated, the harness 100 includes a plurality of straps. In particular, this embodiment is illustrated as having shoulder straps 108A and 108B, front straps 122A and 122B, chest straps 124A and 124B, back straps 120A and 120B, hip strap 116, seat strap 130 and leg straps 110A and 110B. The straps 108A, 108B, 122A, 122B, 124, 120A, 120B, 116, 110A and 110B can generally be referred to as webbings 108A, 108B, 122A, 122B, 124, 120A, 120B, 116, 110A and 110B. The straps or webbings 108*a*, 108B, 122A, 122B, 124, 120A, 120B, 112, 116, 110A and 110B are secured around a user's body. In particular, the shoulder webbings 108A and 108B are positioned around the user's shoulders. The back webbings 102A and 120B are positioned along a back of the user. The front webbings 122A and 122B are positioned along a front of a user. The hip webbing 116 is secured around a waist of the user. The chest webbing 124A and 124B are coupled across a chest of a user with connectors 124A and 124B. Moreover, the leg webbings 110A and 110B are strapped around the legs of the user and coupled in place with leg connectors 109A and 109B and 111A and 111B respectfully. As illustrated in FIG. 1, webbings 122A, 108A and 120B are portions of a single webbing and webbings 122B, 108B and 120A are also portions of a single webbing used to form the harness 100.

The fall protection harness 100 of FIG. 1 also includes a back pad 105 and a hip pad 102. The pads 105 and 102 provide a cushioning between select webbings 108A, 108B 120A, 120B, 122A, 122B and 116 and the user. Coupled to straps 108A and 120B and 108B and 120A proximate the back pad 104 of embodiment of FIG. 1 is a D-ring 103. In use, the D-ring 103 is secured to a support structure with a lanyard of lifeline to provide fall protection and to prevent the user from falling to the ground if an accident occurs. As illustrated, the shoulder straps 108A and 108B are threaded through a retaining aperture 132 in the D-ring 103. Also illustrated in FIG. 1 are work positioning D-rings 118A and 118B coupled to the hip webbing 116. The work positioning D-rings 118A and 118B are used as attachments points when positioning a user in a desired work position.

In embodiments of the present invention, protection members such as protection members 104A, 104B, 104C and 104D associated with hip pad 102 and protection members 106A and 106B associated with back pad 105 are used. Each of the protective members 104A, 104B, 104C, 104D, 106A and 106B protects associated webbing from wear and abrasions. The protective members 104A, 104B, 104C, 104D, 106A and 106B are further described below.

Figure 2A:
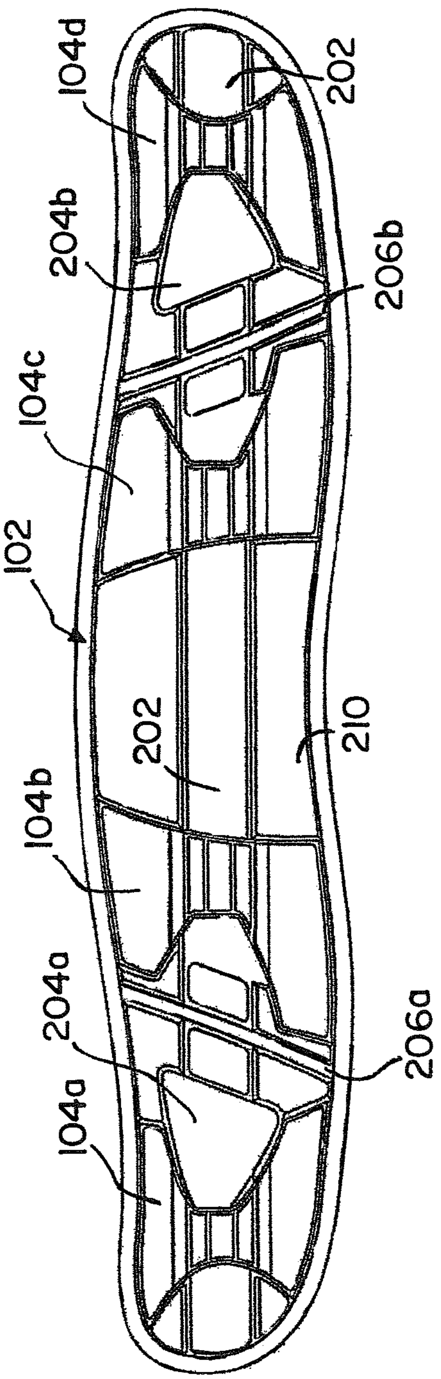
FIG. 2A is a front view of a hip pad of one embodiment of the present invention.
Figure 2B:
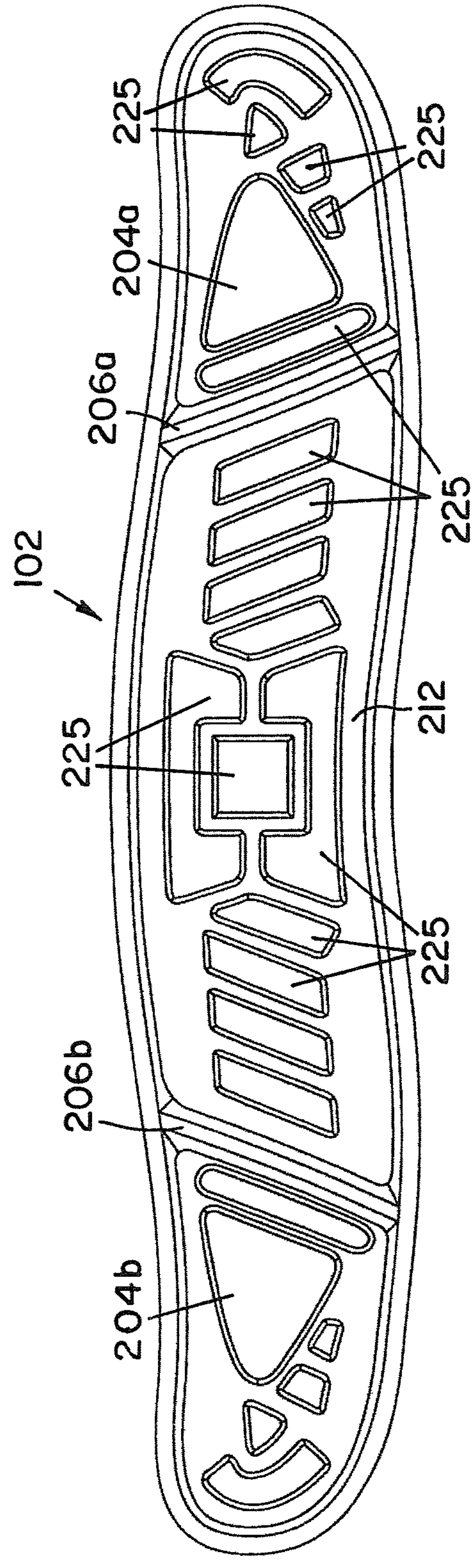
FIG. 2B is a back view of the hip pad of FIG. 2A.

Referring to FIG. 2A, a front view of a hip pad 102 of one embodiment is illustrated. The hip pad 102 is made from a flexible material such as but not limited to compression molded foam. In one embodiment, a fabric cover is placed over at least portions of the compressed foam. An example of one type of fabric used is nylon. Other types of fabric can also be used. The hip pad 102 is illustrated as having a channel guide 202 and protective members 104A, 104B, 104C and 104D. Also illustrated in FIG. 2A are flexible portions 206A and 206B. The flexible portions 206A and 206b are made from a material that assists the hip pad 102 to bend around a waist of the user. In one embodiment, the flexible portions 206A and 206B are made from a fabric strip. In the embodiment of FIG. 2A, the hip pad 102 has openings 204A and 204B that provides ventilation. FIG. 2B illustrates a back view of the hip pad 102. The back view illustrates a first side 212 of the hip pad 102 that is designed to engage the waist of the user. As illustrated, the first side 212 of the hip pad 102 includes spaced protrusions that provide padding and ventilation. A second side 210 of the hip pad 102 is illustrated in FIG. 2A.

Figure 3A:
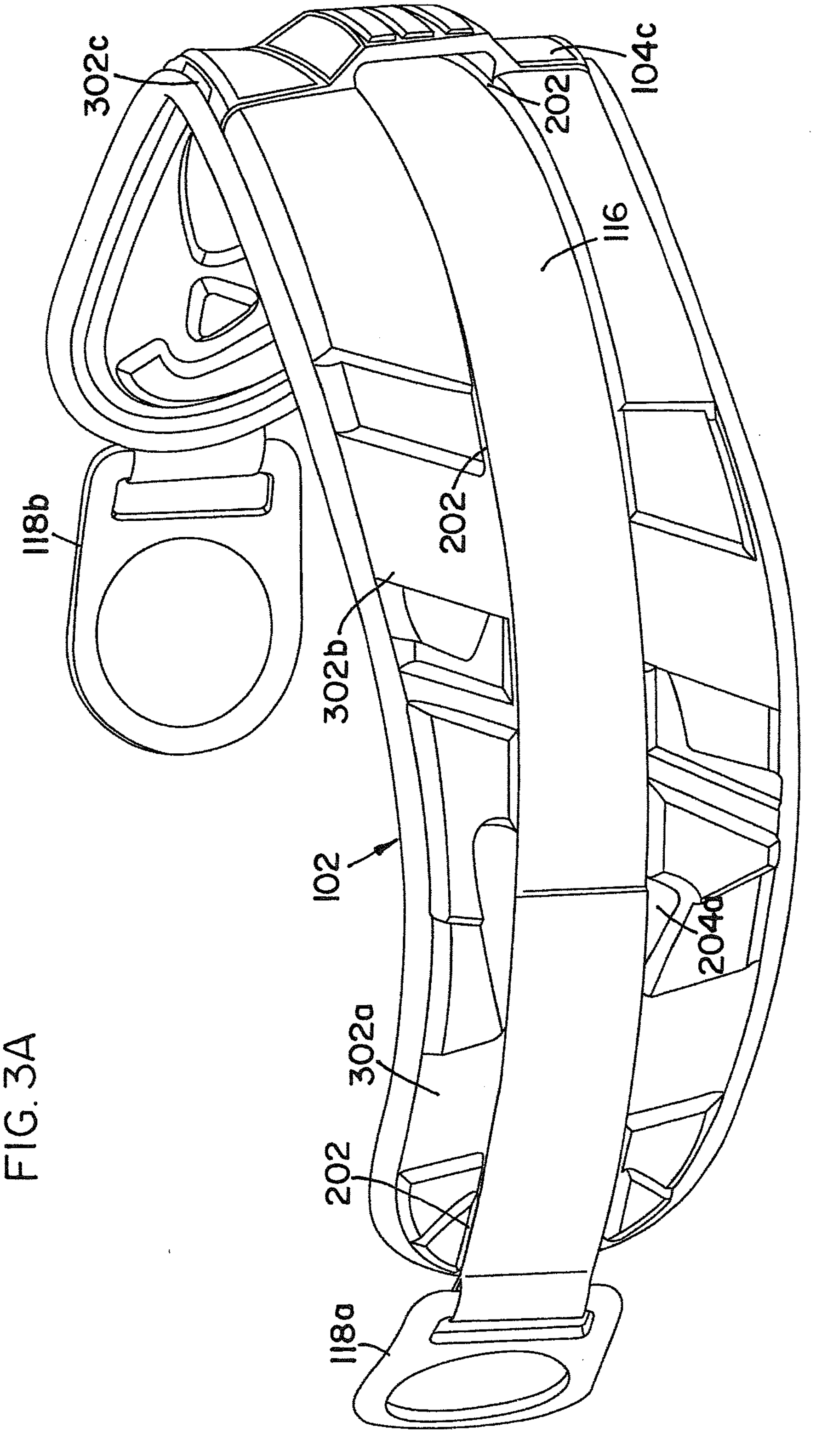
FIG. 3A through 3C illustrate the positioning of straps and protective members on a front perspective view of a hip pad of one embodiment of the present invention.
Figure 3B:
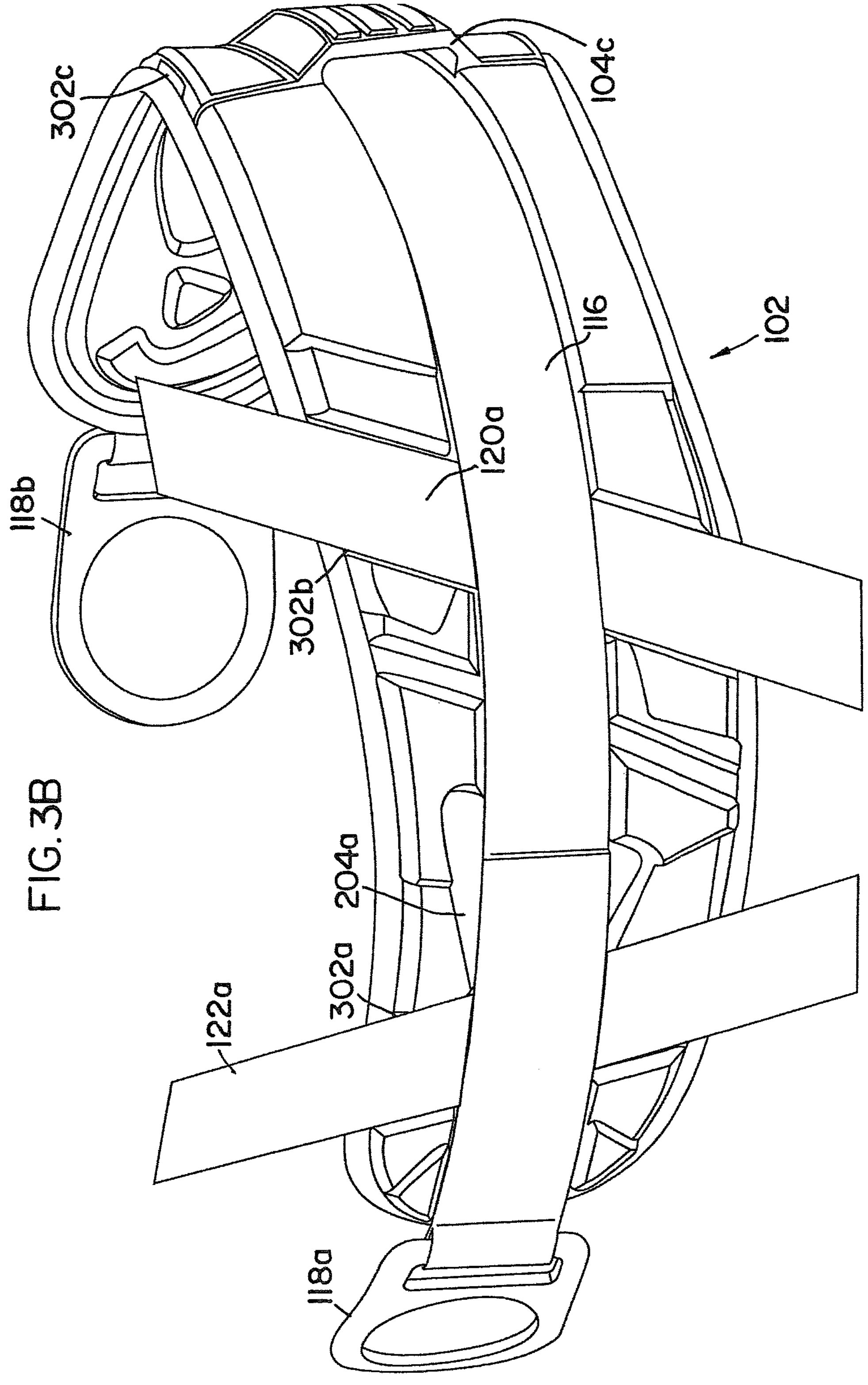
Figure 3C:
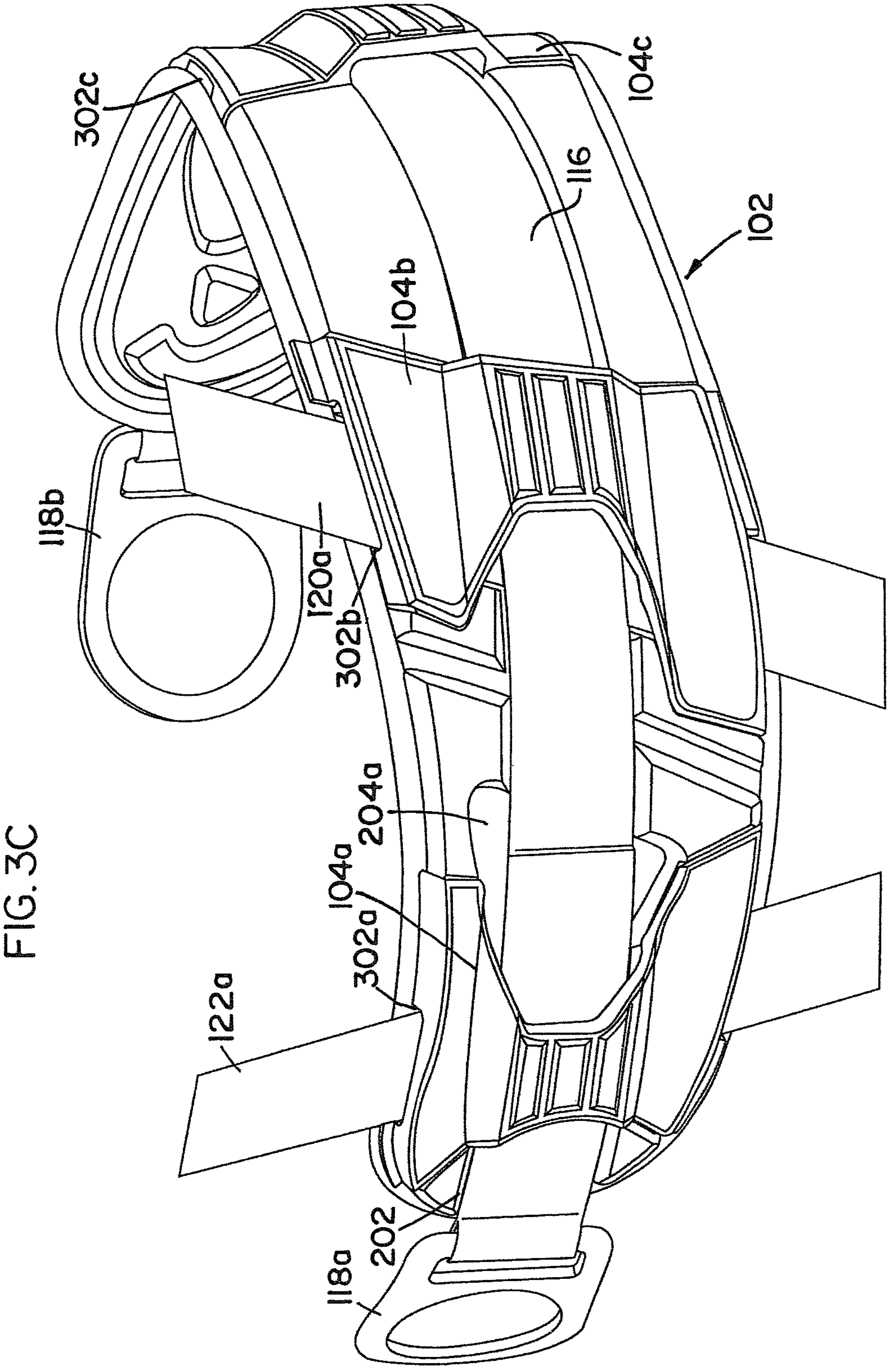

FIGS. 3A through 3C show front perspective views of the hip pad 102 illustrating the placement of webbings 116, 122A and 120A and protective members 104A and 104B of one embodiment. The placement is illustrated with regard to one side, the other side is similarly assembled. Referring to FIG. 3A, hip webbing 116 is illustrated as being positioned in channel guide 202. As illustrated, the hip pad 102 in this view also includes guide channels 302A, 302B and 302C. FIG. 3B, webbing 122A is illustrated as being positioned in channel guide 302A and webbing 120A is illustrated as being positioned in channel guide 302B. Although not shown, webbing 120B would be received in channel guide 302C and webbing 122B would also be received in an associated channel guide (not shown in this view) in this embodiment. FIG. 3C illustrates how protective members 104A and 104B fit over the respective guide channels 202, 302A and 302B to form channel paths. The respective webbings 116, 122A and 120A are received in the respective channel paths. The attachment of a protective member and the webbing to a hip pad is further described below.

Figure 4A:
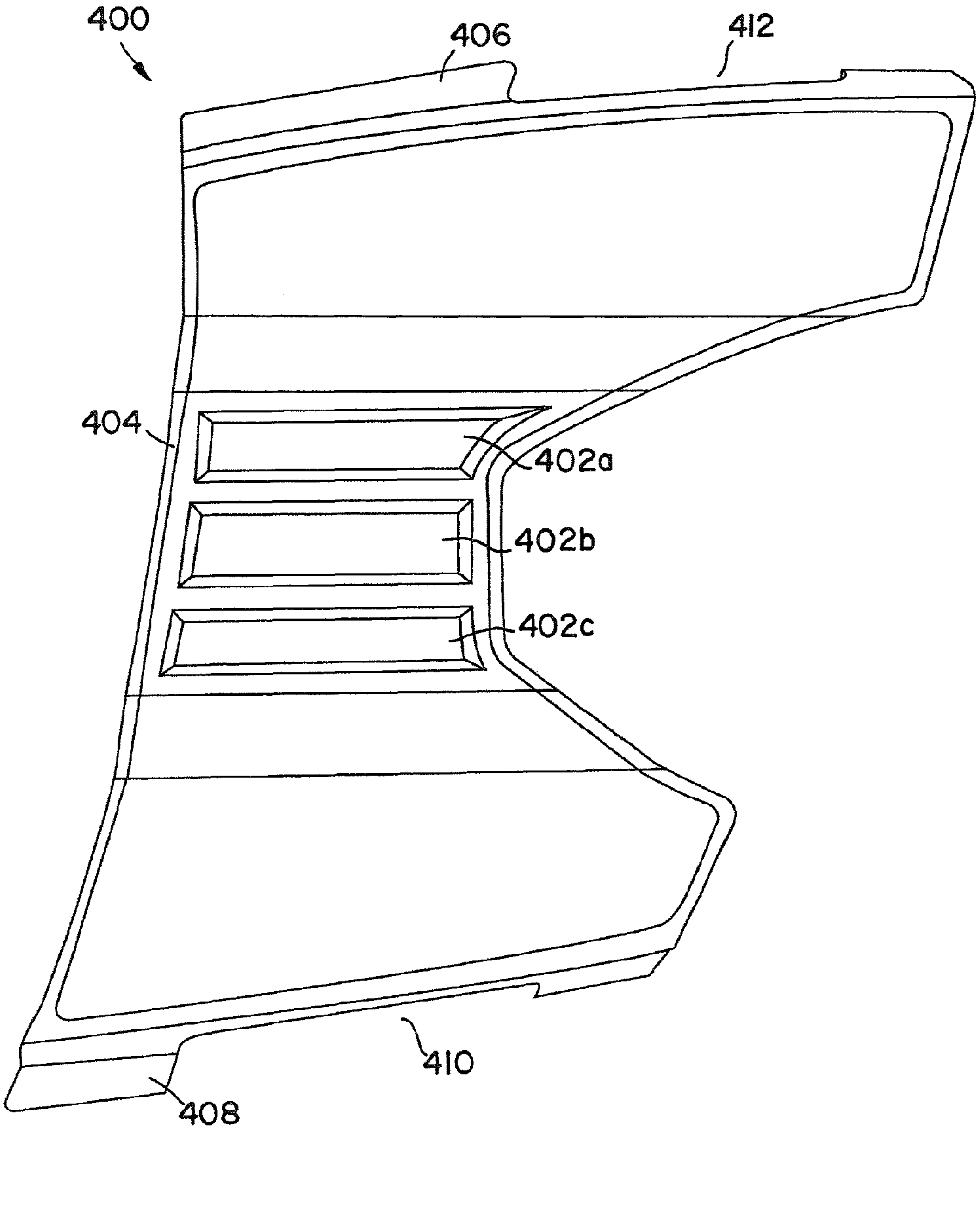
FIG. 4A is a front view of a protection member of one embodiment of the present invention.
Figure 4B:
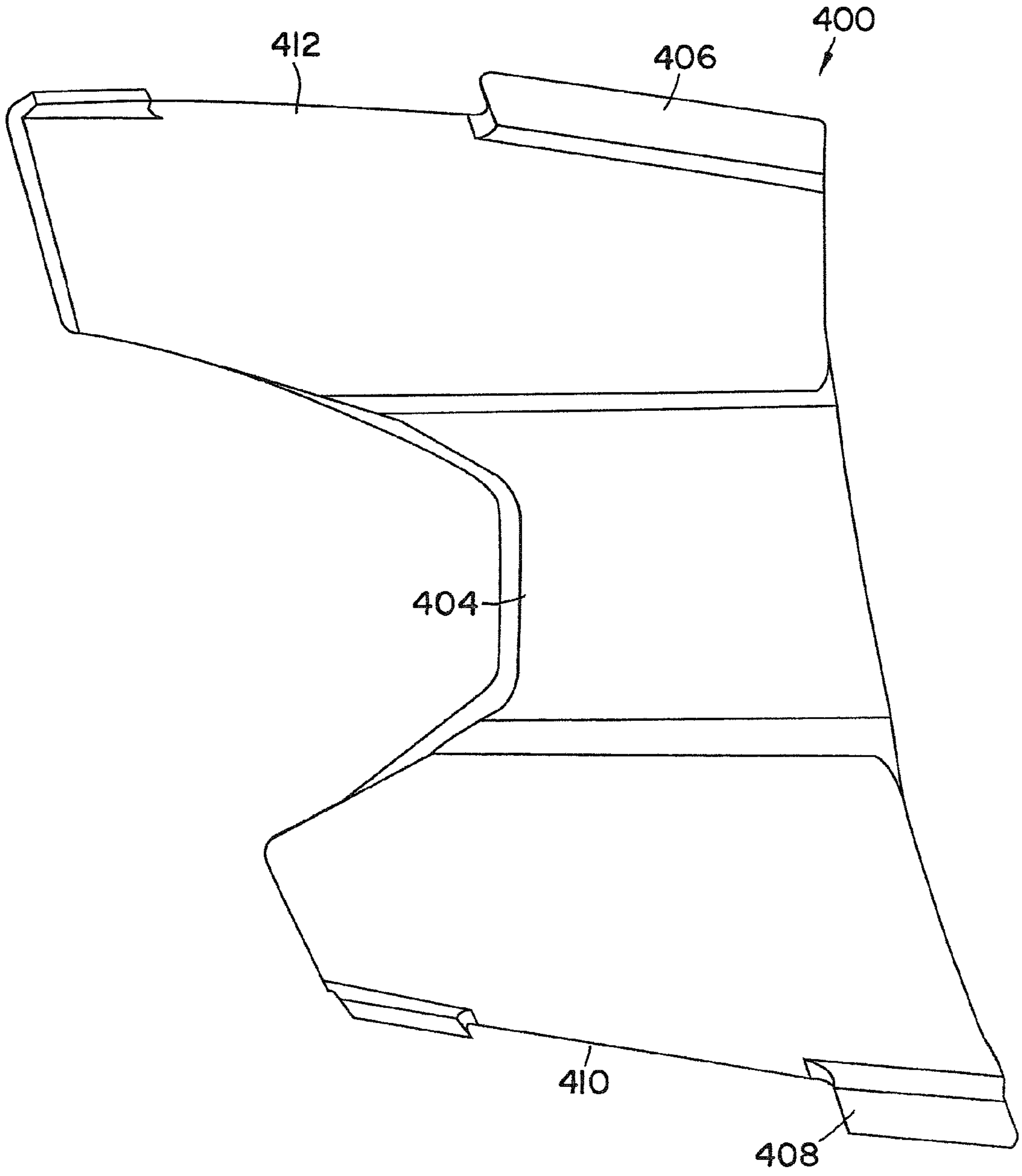
FIG. 4B is a back view of the protection member of the embodiment of FIG. 4A.

Referring to FIGS. 4A and 4B, an illustration of a protective member 400 of one embodiment is illustrated. In particular, FIG. 4A illustrates a front view of protective member 400 and FIG. 4B illustrates a back view of protective member 400. As illustrated, the protective member 400 includes attaching portions (or attaching tabs) 406 and 408 that are used to be attached to the hip pad 102. Each protective member 400 includes a raised portion 404 which provides a guide path for a respective webbing to pass through. Hence, in some embodiments, protective members 400 act like belt loops to retain the webbing. In the protective member 400 embodiment of FIGS. 4A and 4B, the protective member further has webbing slots 410 and 412 that provide a second webbing path that crosses the guide path of the raised portion 404. As FIG. 4A illustrates, in an embodiment the raised portion 404 further includes raised ridges 402A, 402B and 402C. The raised ridges 402A, 402B and 402C provide added wear member material to protect the webbings at locations prone to wear. In addition, the raised portion 404 and raised ridges 402A, 402B and 402C prevent objects from contacting the hip pad 102 to help prevent wear of stitching on the webbing as well as the webbing and pads themselves. In one embodiment, the protective members 400 are made from thermal polyurethane (TPU) material.

Figure 5A:
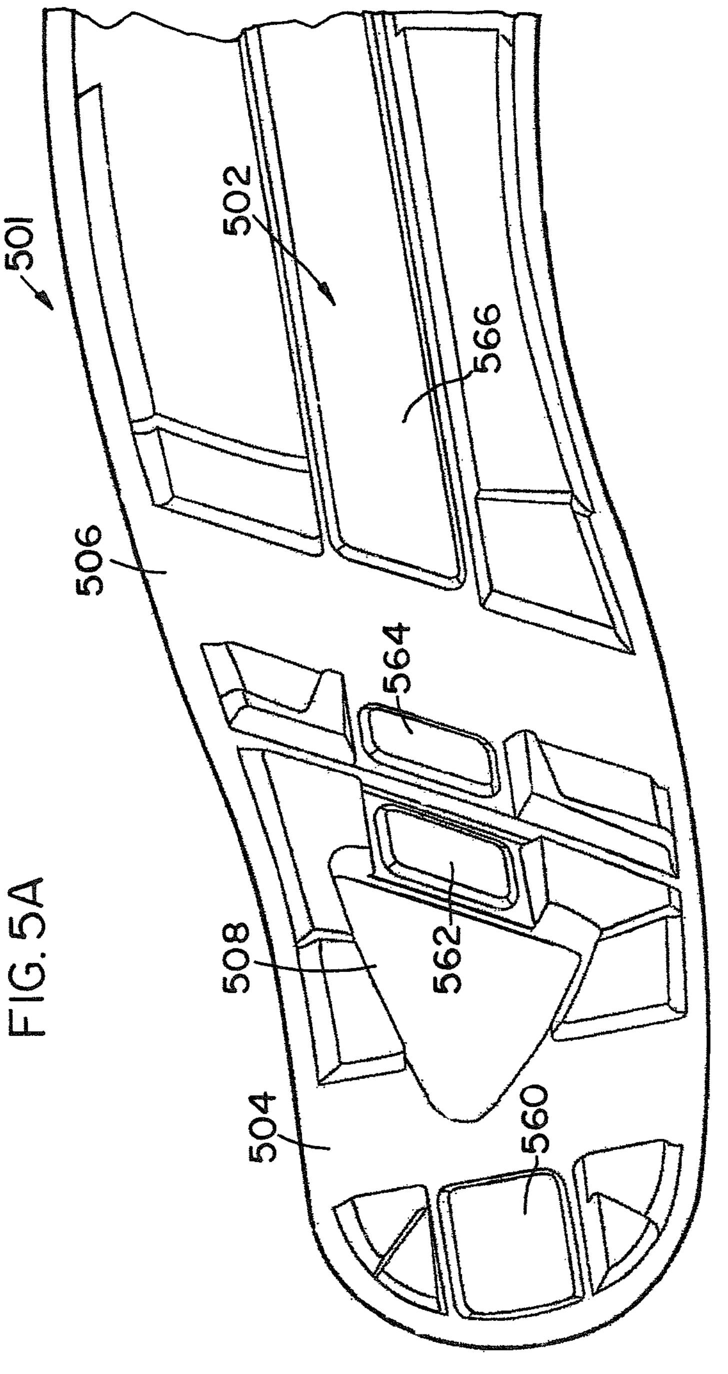
FIGS. 5A through 5E illustrate one method of placing straps and attaching protection members of an embodiment of the present invention.
Figure 5B:
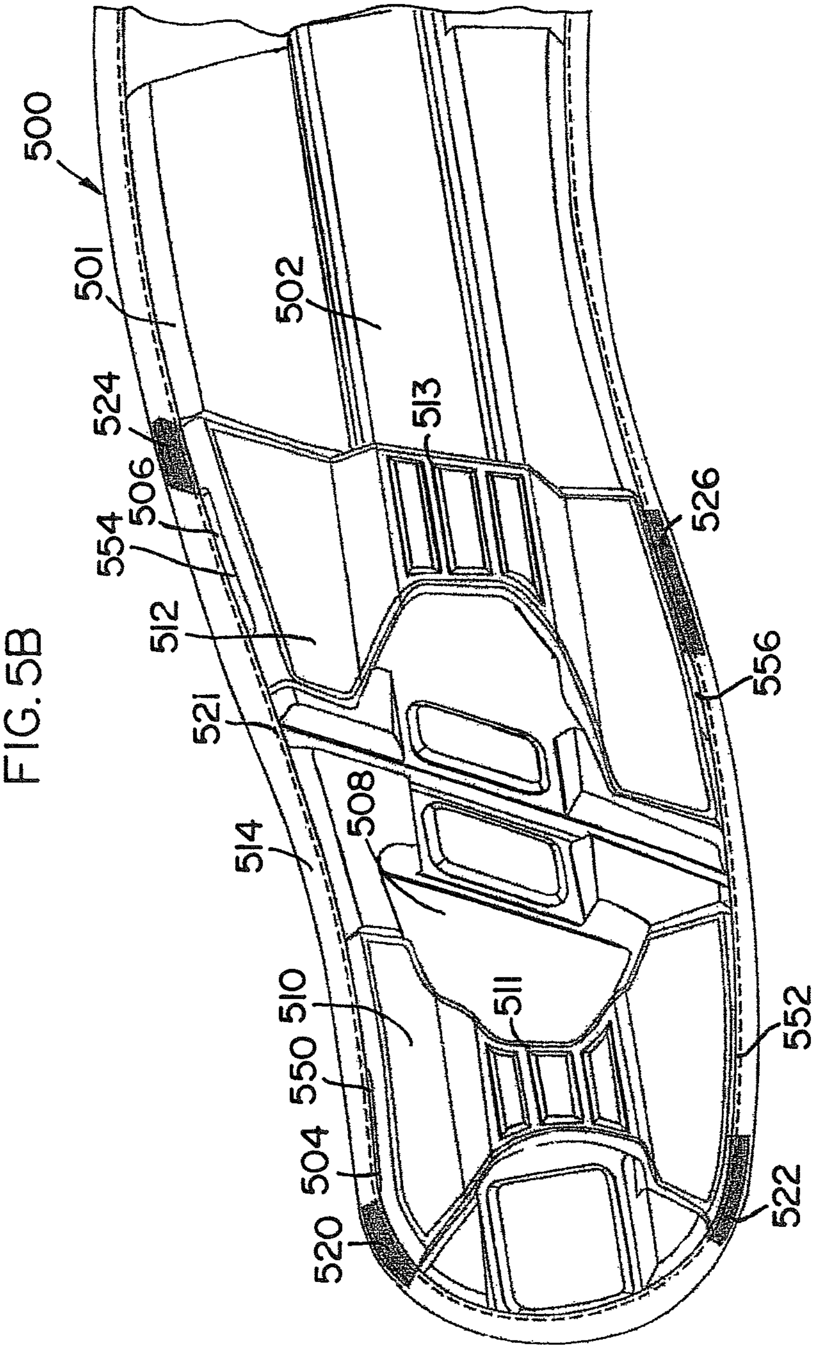
Figure 5C:
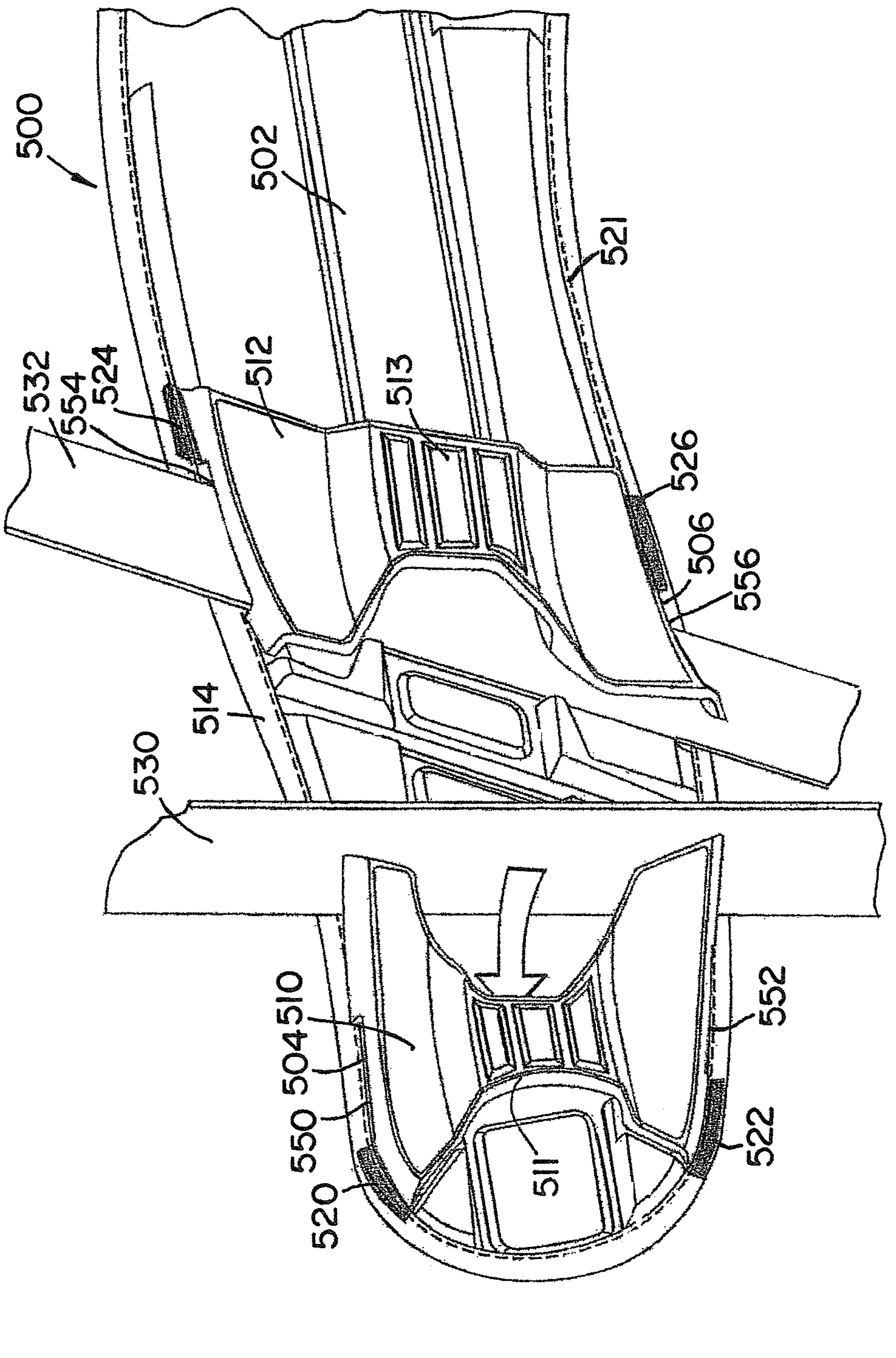

The attachment of protective members to a hip pad 500 of one embodiment is illustrated in FIGS. 5A through 5C. Referring to FIG. 5A, an illustration of a compressed padding member 501 of a hip pad without a binding, webbings and protective members is shown. The sleek compressed padding member 501 is made from a material such as but not limited to compression molded foam as discussed above. As illustrated, this compressed padding member 501 includes a first channel guide 502, a second channel guide 504 and a third channel guide 506. The first channel 502 has raised portions 560, 562, 564 and 566. The raised portions 560, 562, 564 and 566 allow a webbing positioned in the first channel 502 to not interfere with intersecting webbings positioned in guide channels 504 and 560. Moreover, in one embodiment the raised portions 560,562, 564 and 566 have a height that relatively corresponds to the thickness of the webbings positioned in guide channels 504 and 560. This arrangement provides a more uniform force on the compressed padding member 501 around a hip of a user with a webbing positioned in the first guide channel 502. Also illustrated in FIG. 5A is an opening 508. The opening 508 allows for breath-ability of a hip pad when in use.

FIG. 5B illustrates a hip pad 500 that includes the compressed padding member 501 and binding 514. In FIG. 5B, the respective protective members 510 and 512 are positioned on the compressed padding member 501. In particular, protection member 510 is positioned on the compressed padding member 501 such that its raised portion 511 is aligned with channel guide 502 of the compressed padding member 501and webbing slots 550 and 552 of the protection member 510 align with channel guide 504. Similarly, protection member 512 is positioned on the compressed padding member 501 such that its raised portion 513 is aligned with channel guide 502 of the compressed padding member 501 and webbing slots 554 and 556 of the protection member 510 align with channel guide 506. Once the protection members 510 and 512 are positioned on the compressed padding member 501, a portion of each protective member 510 and 512 is connected to the compressed padding member 501 as illustrated in FIG. 5B. In particular, regarding protective member 510, attaching tabs 520 and 522 of protective member 510 are positioned between the compressed padding member 501 and the binding 514. Similarly, tabs 524 and 526 of protective member 512 are positioned between the compressed padding member 501 and the binding 514. The compressed padding member 501 and the binding 514 are then coupled together by stitching 521 to from the hip pad 500. The stitching 521 also couples the outer connection flanges 520 and 522 of the first protective member 510 and the outer flanges 524 and 526 of the second protective member 512 to the hip pad 500.

Figure 5D:
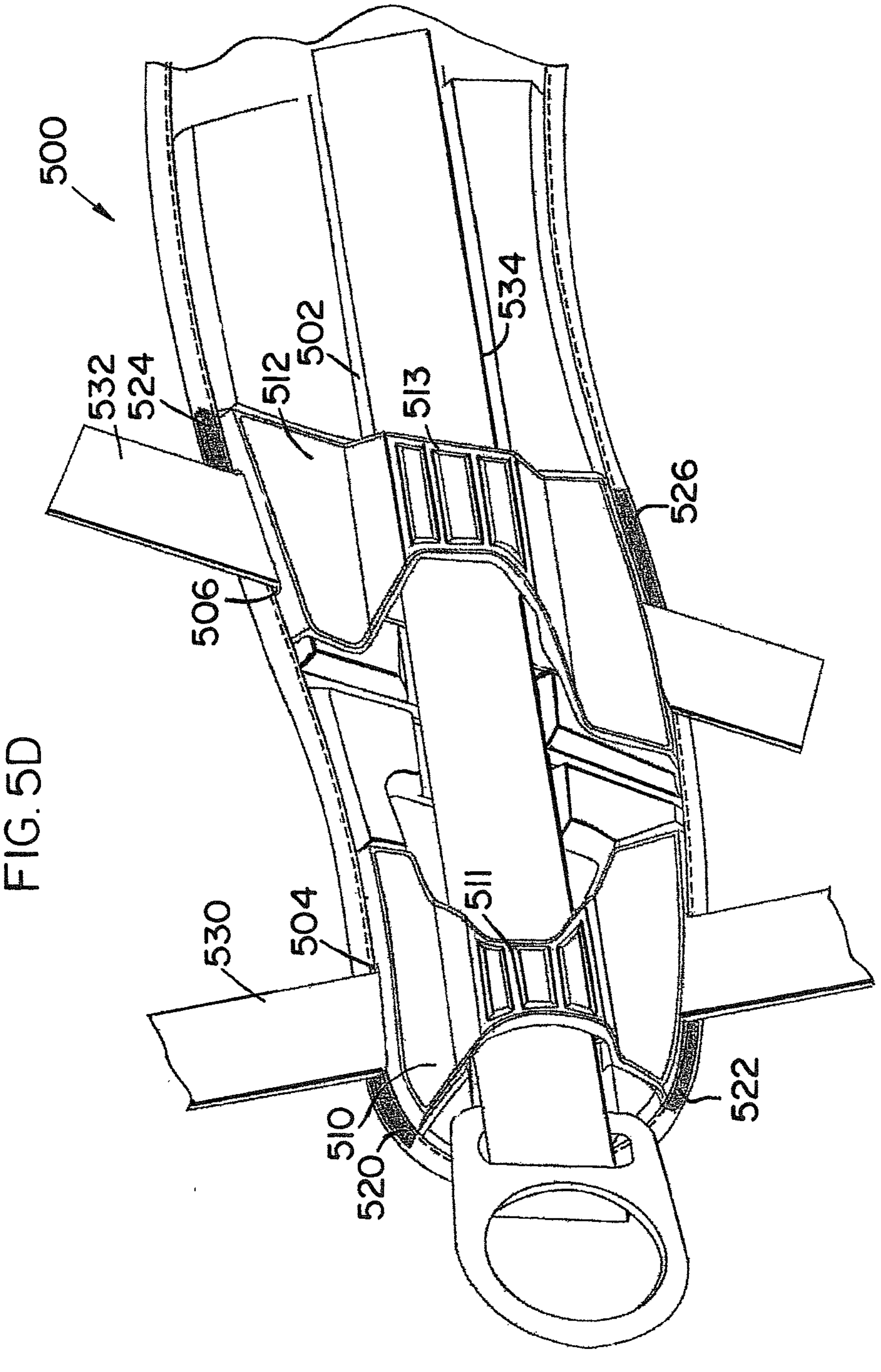
Figure 5E:
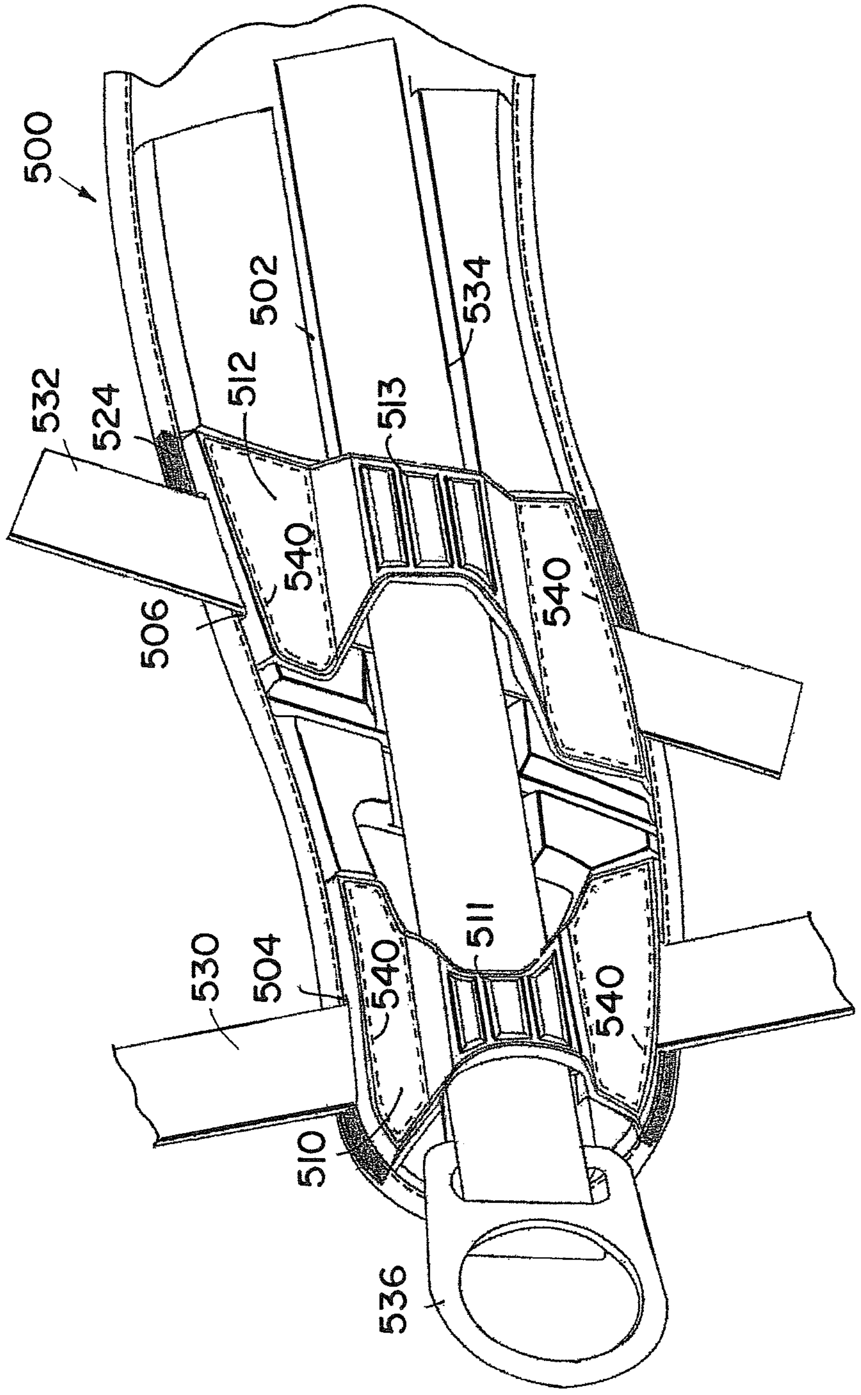

Once a portion of each protective member, protective members 510 and 512 in this example, are connected to the hip pad 500, webbings, such as webbings 530 and 532, are positioned in the respective channel paths made by respective channel guides 504 and 506 in the hip pad 500 and the webbing slots 550, 552, 554 and 556 of the protection members 510 and 512 as illustrated in FIG. 5C. A third webbing (the hip webbing 534) is then positioned in the channel path made by the channel guide 502 of the hip pad 500 and the raised portions 511 and 513 of the protective members 510 and 512 as illustrated in FIG. 5D. Once each of the webbings 530, 532 and 534 is in its respective channel path, the protective members 510 and 512 are fully connected to the hip pad 500 as illustrated in FIG. 5E. In the embodiment of FIG. 5E, stitching 540 is used to couple the protective members 510 and 512 to the hip pad 500. In one embodiment, the stitching 540 passes through webbings 530 and 532 to retain the webbings 530 and 532 at a static position with regard to the hip pad 500 and retaining members 510 and 512. Stitching 540 also prevents D-ring 536 from passing through protective member 510. A similar arrangement on another end of the hip pad (not shown) retains webbing 536 in the hip pad 500. The raised portions 511 and 513 of the protection members 510 and 512 helps protect the stitching 540 from wear by preventing objects from rubbing against the stitching 540.

Figure 6:
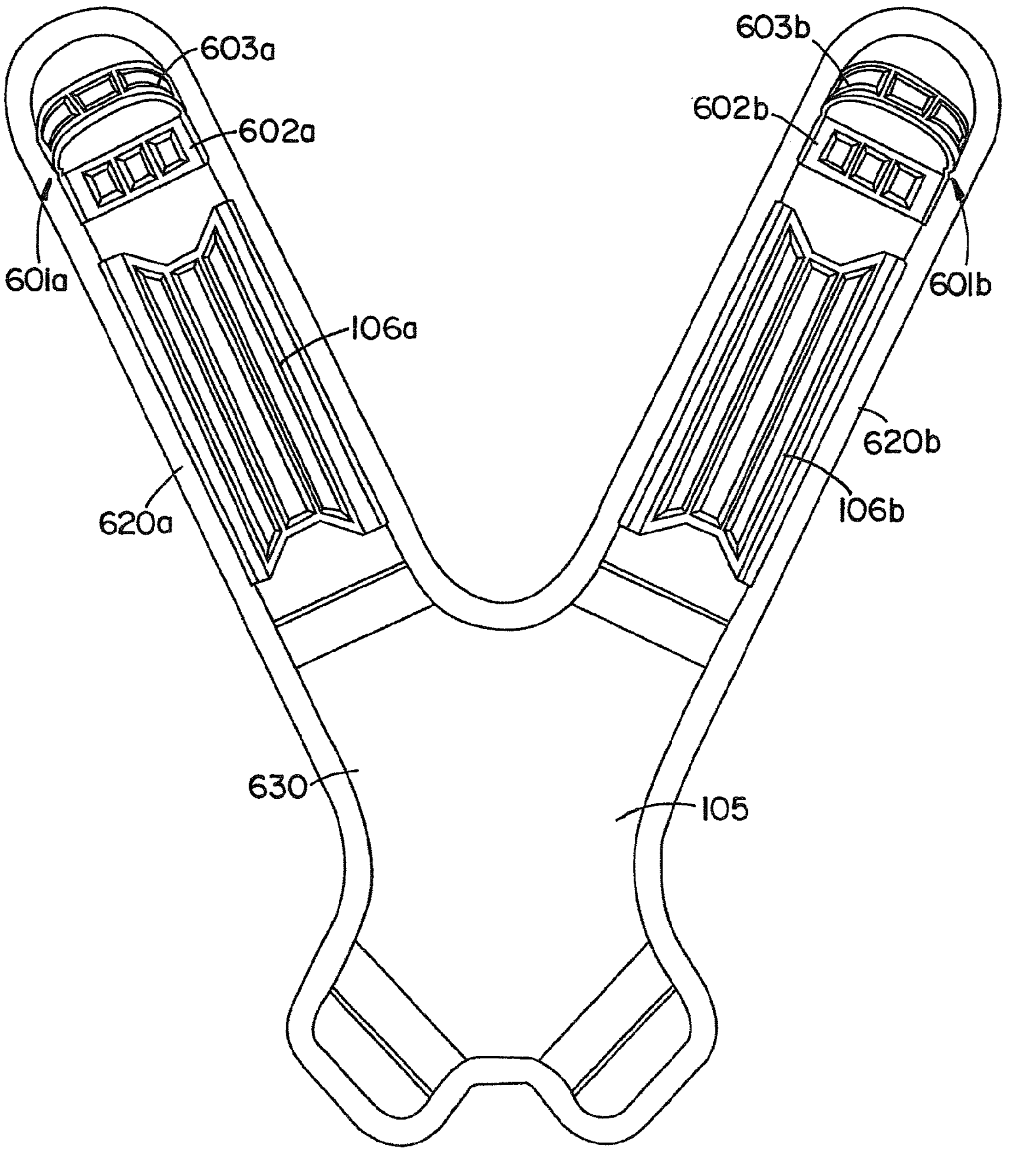
FIG. 6 is a front view of a back pad of one embodiment of the present invention.
Figure 7B:
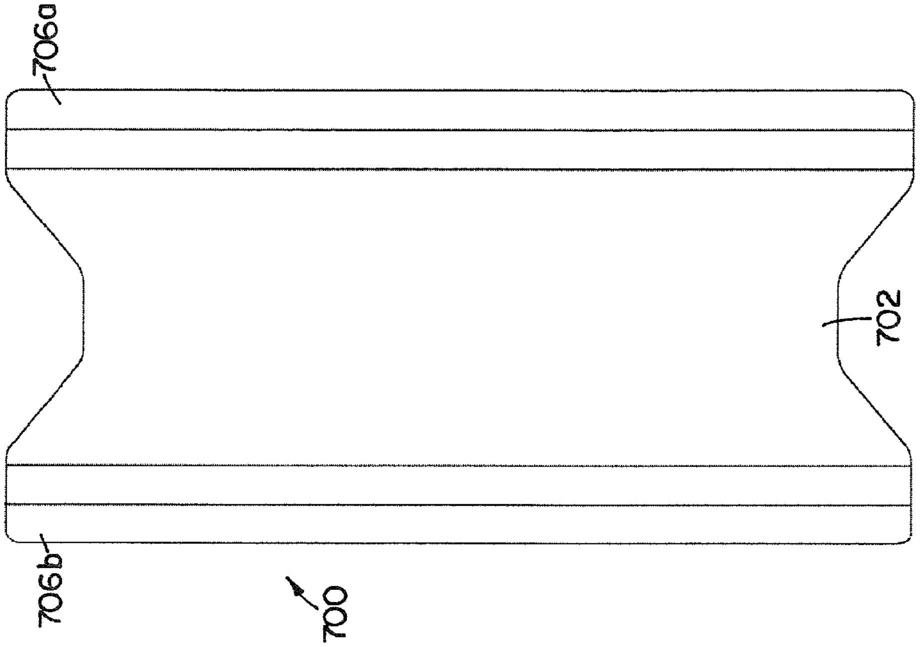
FIG. 7B is a back view of the protection member of embodiment of FIG. 7A.
Figure 7A:
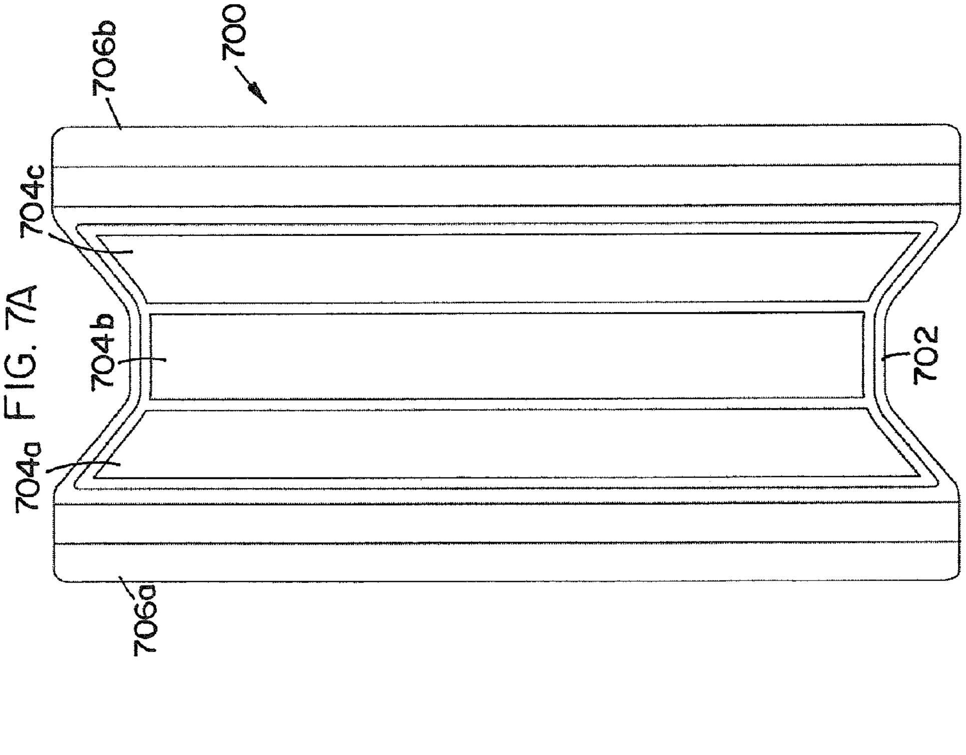
FIG. 7A is a front view of protection member of another embodiment of the present invention.

An example of protective members 106A and 106B for the shoulder webbings is illustrated in FIG. 6. FIG. 6 is a front view of protective members 106A and 106B and lanyard systems 601A and 601B. Each lanyard systems 601A and 601B is attached to a respective shoulder pad portion 620A and 620B of the back pad 105. The lanyard systems 601A and 601b include guide portions 602A and 602B that provide a guide path for select shoulder webbing 108A or 108B. The lanyards systems 601A and 601B further comprise attaching portions 603A and 603B used for tool connections. Also illustrated in FIG. 6 is the dorsal pad portion 630 of the back pad 105. An illustration of a protective member 700 used with the shoulder pad portions 620A and 620B of the back pad 105 is illustrated in FIGS. 7A and 7B. In particular, FIG. 7A is a front view of the protective member 700 and FIG. 7B is a back view of the protective member 700. The protective member 700 includes connections portions 706A and 706B that are coupled to the back pad 105 proximate the respective shoulder pad portions 620A and 620B. The protective member 700 has a raised portion 702 which provides a guide path for associated webbing. The protective member 700 further has a plurality of raised ridges 704A, 704B and 704C on the raised portion 702 that provide for extra wear members.

Figure 8:
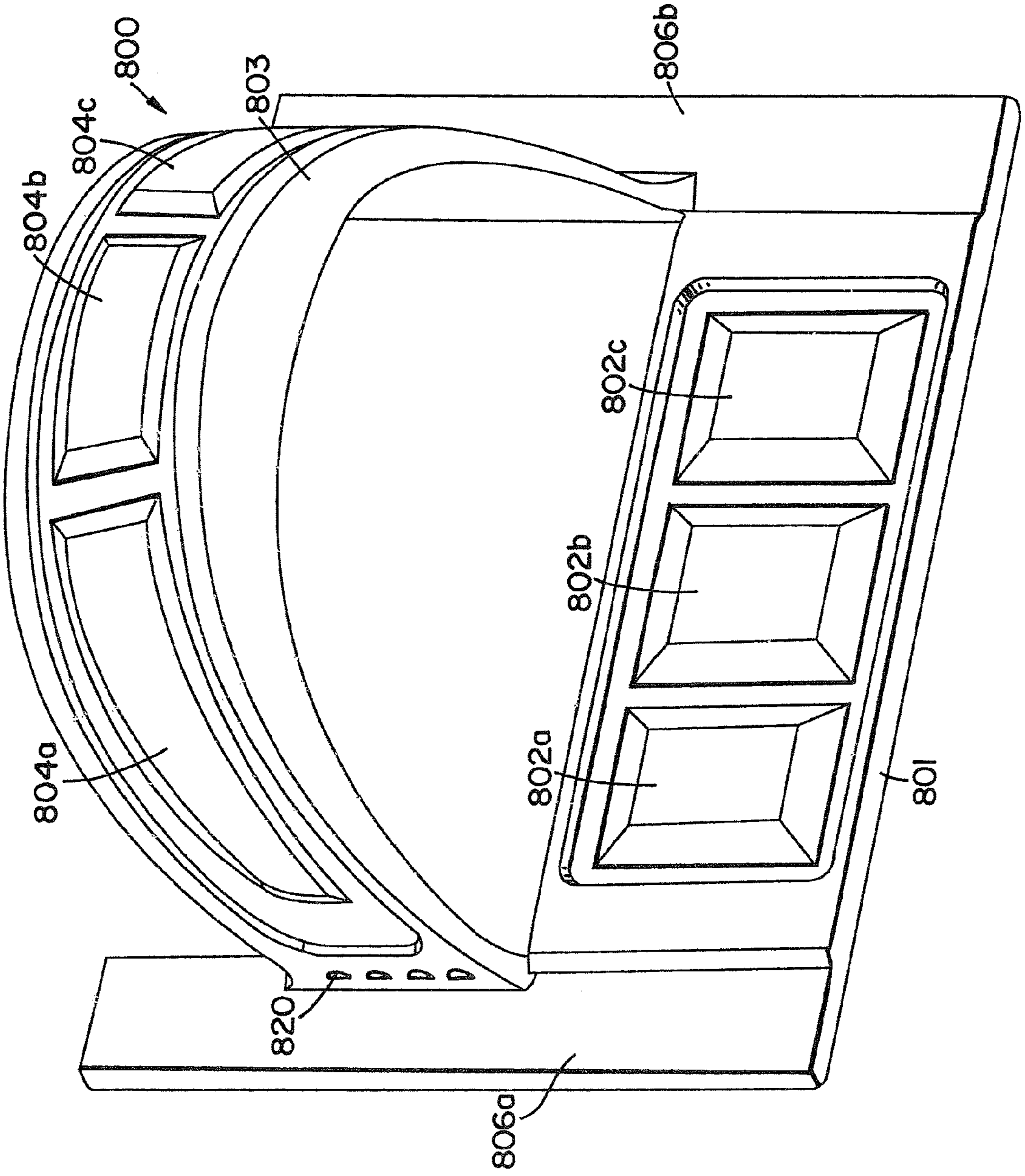
FIG. 8 is a front perspective view of a lanyard system of one embodiment of the present invention.

Referring to FIG. 8, a front perspective view of a lanyard system 800 of one embodiment is illustrated. The lanyard system 800 includes a guide portion 801 and an attaching portion 803. The lanyard system 800 further includes connecting portions 806A and 806B that are coupled to a back pad, such as back pad 105 of FIG. 1, proximate the shoulder pad portions 620A and 620B. The respective shoulder strap 108A or 108B is positioned between the guide portion 801 and the back pad 105. The guide portion 801 is a raised from the connecting portions 806A and 806B so that a guide path is formed between the back pad 105 and the guide portion 801. The guide portion 801 in this embodiment includes raised ridges 802A, 803B and 803C that provide added material to protect the webbing 108A or 108B. The attaching portion 803 is used to attach tools and equipment thereto with connectors such as with relatively large snap hooks, carabiners and the like. The attachment portion 803 of the lanyard system 800 in this embodiment includes raised ridges 804A 804B and 804C. In one embodiment, the attachment portion 803 is designed to at least partially break away from the lanyard system 800 when a select amount of force is applied. This prevents the attachment portion 803 from interfering with the user's task if the attachment portion 803 (or a tool attached to the attachment portion 803) gets unintentionally hooked or caught on something. In one embodiment, the breakaway attachment is done with perforations 820, or the like, that provide a weakened area.

Figure 9:
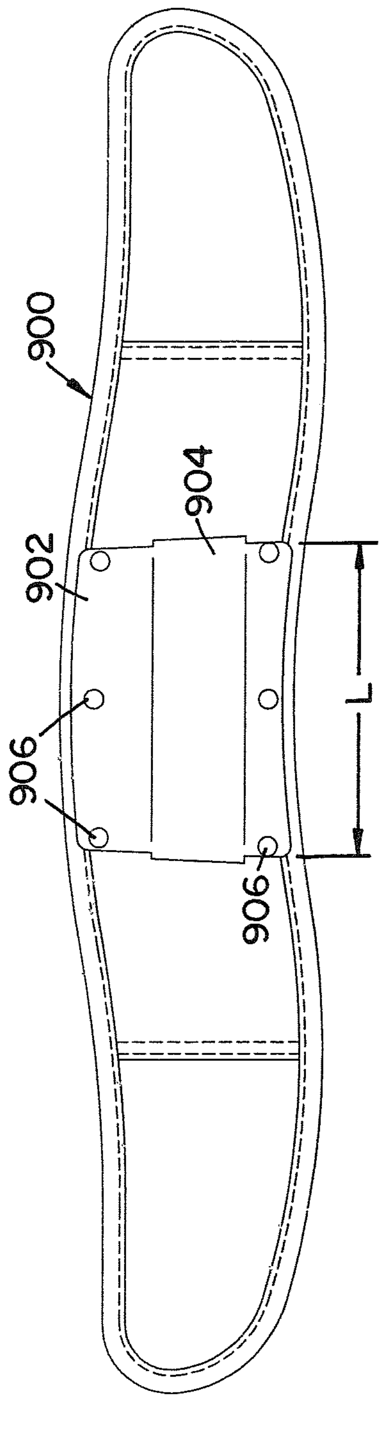
FIG. 9 is an illustration of another embodiment of a hip pad and protective member of the present invention.
Figure 10B:
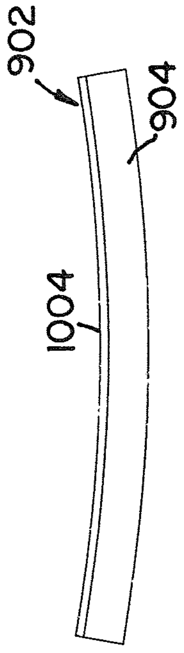
FIG. 10B is a top view of the protective member of FIG. 9.
Figure 10A:
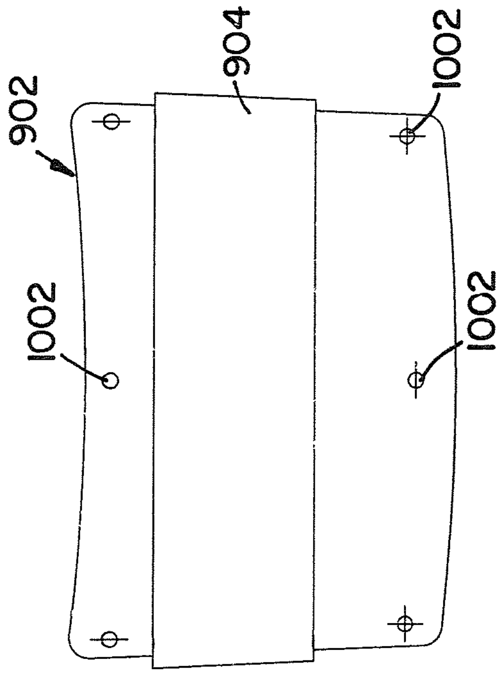
FIG. 10A is a front view of the protective member of FIG. 9.

FIG. 9 illustrates an embodiment of another embodiment of a hip pad 900 of the present invention. This hip pad 900 can be used in the harness 100 of FIG. 1 instead of hip pad 102. Hip pad 900 includes protection member 902. As illustrated, protection member 902 is coupled to the hip pad 901 via connectors 906 such as but not limited to rivets. Protection member 902 in this embodiment has a raised portion 904 in which the hip webbing passes through. This is similar to hip webbing 116 passing through protective members 104A, 104B, 104C and 104D of FIG. 1. The raised portion 906 of the protection member 902 prevents objects from touching the hip webbing 905 thereby preventing wear of the webbing 905. In one embodiment, the protection member 902 is made from a lightweight thermoplastic. In the embodiment of FIG. 9, the protection member 902 has a length L that is less than a width of a user's back. Hence, the remainder of the hip pad 901 is able to bend around the user's back. Moreover, limiting the length L of the protection member 902 keeps down the overall weight of the protection harness 900. FIGS. 10A through 10C further illustrate protection member 902. In particular, FIG. 10A illustrates a front view of the protection member 902. As illustrated, the protection member 902 includes apertures 1002 which allow for the connectors 906 to connect the protection member 902 to the back pad 900. A top view of the protection member 902 is illustrated in FIG. 10B. As illustrated, the protection member 902 in this embodiment has a curve. The side view of the protection member 902 of FIG. 10C illustrates, the protection member 902 has a first side configured to engage a hip pad and a second side 1006 that provides wear protection. Also, illustrated in FIG. 10C is the raised portion 904 that along with the hip pad 900 provides a channel path for the webbing and provides wear protection for the webbing and the hip pad.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

The invention claimed is:

1. A webbing protection system comprising:

at least one pad portion having a first pad surface and a second pad surface, the first pad surface of each pad portion configured to engage a portion of a body of a user, the second pad surface having at least a first pad channel guide and a second pad channel guide, the second pad channel guide intersecting the first pad channel guide;

at least one protective member having at least one raised portion, the at least one protective member coupled to the at least one pad portion such that the raised portion of the protective member is aligned with the first pad channel guide of the associated pad portion to provide a first guide path for the first webbing, the at least one protective member providing wear and abrasion protection for a first webbing; and the at least one protective member further forming a second guide path for a second webbing with the second pad channel guide of the at least one pad portion, wherein the first guide path for the first webbing and the second guide path for the second webbing intersect each other.

2. The webbing protection system of claim 1, further comprising:

the at least one protective member having a first protective surface and a second protective surface, at least a portion of the first protective surface of the at least one protective member configured to engage the second pad surface of an associated pad portion.

3. The webbing protection system of claim 2, wherein the second protective surface of the at least one protective member has at least one raised ridge.

4. The webbing protection system of claim 1, wherein the at least one pad portion further comprises:

a first end pad portion;

a second end pad portion; and a mid section pad portion positioned between the first end pad portion and the second end pad portion; the first end pad portion, the second end pad portion and the mid section pad portion flexibly coupled together.

5. The webbing protection system of claim 4, wherein the first end pad portion is coupled to the mid section portion with a first fabric strip and the second end pad portion is coupled to the mid section pad portion with a second fabric strip.

6. The webbing protection system of claim 4, wherein the at least one protective member further includes a first and a second protective member, the first and second protective members coupled to the mid section pad portion such that the at least one raised portion of the first and second protective members are aligned with the at least one channel guide of the mid section portion to provide the first guide path for the first webbing.

7. The webbing protection system of claim 1, wherein the pad portion is a hip pad.

* * * * *